(12) United States Patent
Kancerevycius et al.

(10) Patent No.: US 11,903,875 B2
(45) Date of Patent: Feb. 20, 2024

(54) GLAUCOMA IMPLANT DEVICE

(71) Applicant: Valsigna GmbH, Lugano (CH)

(72) Inventors: Gitanas Kancerevycius, Ponte Capriasca (CH); Linas Jonusauskas, Vilnius (LT); Valdas Monkus, Vilnius (LT)

(73) Assignee: Valsigna GmbH, Lugano (CH)

( * ) Notice: Subject to any disclaimer, the term of this patent is extended or adjusted under 35 U.S.C. 154(b) by 5 days.

(21) Appl. No.: 17/523,047

(22) Filed: Nov. 10, 2021

(65) Prior Publication Data

US 2023/0146222 A1     May 11, 2023

(30) Foreign Application Priority Data

Nov. 9, 2021   (EP) .................... 21207254

(51) Int. Cl.
   *A61F 9/007*    (2006.01)
   *A61F 2/00*     (2006.01)
   *A61F 2/14*     (2006.01)

(52) U.S. Cl.
   CPC ........ *A61F 9/00781* (2013.01); *A61F 2/0063* (2013.01); *A61F 2/14* (2013.01); *A61F 2002/0068* (2013.01)

(58) Field of Classification Search
   CPC ...... A61F 9/00781; A61F 2/0063; A61F 2/14; A61F 2002/0068
   See application file for complete search history.

(56) References Cited

U.S. PATENT DOCUMENTS

| | | | |
|---|---|---|---|
| 2018/0325731 A1* | 11/2018 | Gross | A61F 9/0008 |
| 2022/0117724 A1* | 4/2022 | Nishizawa | G02C 7/04 |
| 2022/0211922 A1* | 7/2022 | Nielsen | A61K 47/42 |

FOREIGN PATENT DOCUMENTS

| | | | | |
|---|---|---|---|---|
| CN | 111772870 A | * | 10/2020 | A61F 2/14 |
| WO | WO-2004033021 A1 | * | 4/2004 | A61B 17/205 |
| WO | WO-2015108970 A1 | * | 7/2015 | A61F 2/15 |
| WO | WO-2018156687 A1 | * | 8/2018 | A61F 2/0063 |
| WO | WO-2019055311 A1 | * | 3/2019 | A61B 17/221 |
| WO | WO-2019190352 A1 | * | 10/2019 | |
| WO | WO-2020018436 A1 | * | 1/2020 | A61F 9/008 |

* cited by examiner

*Primary Examiner* — Megan Y Wolf
*Assistant Examiner* — Yasniary De La Caridad Morales
(74) *Attorney, Agent, or Firm* — Jason Lee DeFrancesco (57) ABSTRACT

The present invention is a glaucoma implant device (1) comprising a connection portion (21) coupled to a mesh portion (11), whereby a first group of outlet ducts and second group of outlet ducts are configured such that the mesh portion (11) has a predefined hydraulic resistance threshold, and a stent portion (31) that dilates the Schlemm canal of an eye and directs aqueous humor to the connection portion (21), further directing aqueous humor into subconjunctival or suprachoroidal space.

15 Claims, 7 Drawing Sheets

GLAUCOMA IMPLANT DEVICE

FIELD OF THE INVENTION

The present invention relates to the field of glaucoma treatment. In particular, the present invention relates to a glaucoma implant device.

BACKGROUND ART

Glaucoma is a chronic disease whose progression closely correlates with increased intraocular pressure (IOP). Its management and control seek to preserve the visual field and is dependent on the possibility to control IOP. Most often glaucoma progresses in the older age, which makes the treatment being required for a median 13-16 years until natural death of the patient. There are a number of options available to physicians for glaucoma management and treatment algorithms are pretty well defined. The first choice is usually topical hypotensive eye drops. However, they put significant demands on patients (especially older aged) for administering compliance and frequently have negative side effects on the eye (such as irritation and inflammation), especially with treatment time passing.

Laser Trabeculoplasty is an effective treatment but its effects last for a relatively short time. Traditional glaucoma surgery is very effective in lowering TOP, but has significant risks related to surgery itself and complications later, followed by a relatively high failure rate (by some studies estimated to be up to 40-50% of cases in 5 years). Trabeculectomy, a bleb based golden standard, relies on ostia made by removal of part of the trabecular meshwork and adjacent structures for drainage into subconjunctival space. Tube based surgery relies on drainage via aqueous shunts which drain via encapsulated plate. Both procedures carry significant intrasurgical and postsurgical complications risk (such as hypo tony), which needs skilled surgeons' intervention and special handling. The failure of both procedures in long term are mostly related to the natural body reaction to heal wounds and to encapsulate foreign bodies. Various studies have demonstrated that pressure of aqueous into subconjunctival space rapidly induces serious fibrotic reaction, which is necessary for bleb to function as resistor on one side, but over time it may lead to increasing encapsulation and subsequent bleb failure. Therefore, in the future, bleb needling or another surgery might be needed for the patient. Since body reaction is highly individual, it is normally difficult to estimate success of the bleb.

These highly probable problems of fibrotic encapsulation and bleb failure in long term and probability of postoperative complications (such as hypotony) puts surgery options to the point of the last resort where potential benefit or absence of options outweighs the risks.

Next to these traditional techniques, minimally invasive glaucoma surgery (MIGS) implants are available as relatively new options filling the gap between drops and traditional surgery. Usually, the MIGS implants are manufactured by using subtractive precision manufacturing techniques, leading to tubular, straight line and round orifice designs. MIGS targeting Schlemm canal can be implanted ab interno, reducing surgery risks. However due to natural episcleral veins back pressure they cannot reduce TOP as effectively as traditional surgery, limiting the range of potential patients. MIGS targeting uveoscleral route of drainage are trying to give more control on subscleral bleb outcome or try to exploit suprachoroidal space. However, the presence of the bleb and/or penetration into the anterior chamber might lead to similar problems as trabeculectomy or to the new ones (such as endothelial cells loss due to presence of implant end in the anterior chamber).

It would therefore be desirable to have device capable of minimizing the drawbacks described above.

In particular, it would be desirable to have a device which could be used for defining a procedure which would potentially allow less risky, earlier (longer lasting) surgery, controllable implantation results, relatively low learning curve for implantation skills and low teens TOP reduction if needed.

Furthermore, it would be desirable to have a device capable of achieving a significant cost saving in production and assembly operations.

SUMMARY OF THE INVENTION

An object of the present invention is to provide a device capable of minimizing the aforesaid problems.

The aforesaid object is achieved by a glaucoma implant device according to the attached claims.

The glaucoma implant device is characterized in that it comprises a connection portion and a mesh portion coupled to each other,
  wherein the connection portion is able to direct aqueous humour from Schlemm canal and anterior chamber to the mesh portion and the mesh portion is able to drain aqueous humour into subconjunctival or suprachoroidal space when the glaucoma implant device is implanted,
  wherein the mesh portion is defined by a plurality of polygonal cells arranged side-by-side in contact to each other according to a predefined number of rows and columns,
  wherein each of the polygonal cells has perimetral sides and a through opening in-between defining a liquid collecting area,
  wherein each of the perimetral sides defines an inner duct, the inner ducts being in hydraulic connection to each other,
  wherein one or more of the inner ducts are in hydraulic connection with the connection portion allowing the directing aqueous humour from Schlemm canal to the mesh portion, and
  wherein each of the polygonal cells is provided with at least an opening at the perimetral side able to connect the inner duct to the liquid collecting area allowing the draining of aqueous humour into subconjunctival or suprachoroidal space by flowing out from the inner ducts to the liquid collecting areas.

The glaucoma implant device according to the present invention is intended to allow significantly reducing the fibrotic encapsulation, while maintaining the direction of aqueous humor from the anterior chamber.

In a further embodiment, each of the polygonal cells is provided with an outlet duct departing from the inner duct and ending with the opening and extending in the liquid collecting area,
  wherein the outlet ducts have different inclinations ranging from 15° to 90° with respect to the perimetral side provided with the opening, and
  wherein the outlet ducts have different lengths and diameters such that to achieve a predefine hydraulic resistance threshold of the mesh portion allowing the draining of aqueous humour into subconjunctival or suprachoroidal space by flowing out from the inner ducts to the respective liquid collecting areas simultaneously.

The parameters of the outlet ducts are modeled mathematically as to achieve desired hydraulic resistance threshold of the mesh portion as a whole and to let aqueous outflow via the whole area of the mesh portion to be done simultaneously.

In a further embodiment, the outlet ducts have a dimension ranging from 2 μm to 20 μm in diameter, preferably from 4 μm to 15 μm, and ranging from 15 μm to 100 μm in length.

In a further embodiment, the mesh portion has a dimension ranging from 1 mm in length and 1 mm in width to 4 mm in length and 4 mm in width, preferably is 2 mm in length and 2 mm in width.

In a further embodiment, the predefined number of rows ranges from 10 to 20, preferably is equal to 14, and the predefined number of columns ranges from 10 to 20, preferably is equal to 13.

In a further embodiment, the mesh portion has a dimension ranging from 10 μm to 50 μm in height, preferably is 20 μm in height,
  wherein the perimetral sides have a dimension ranging from 15 μm to 40 μm in width, preferably is 20 μm in width, and
  wherein the diameter of the inner ducts ranges from 5 μm to 12 μm, preferably is equal to 8 μm.

In a further embodiment, the dimension of the openings range from 4 μm to 10 μm, preferably from 5 μm to 8 μm.

In a further embodiment, the polygonal cells have hexagon shape devoid of basis such as to define the through opening in-between and, in turn, the liquid collecting area.

In a further embodiment, the mesh portion has a hexagon periodicity ranging from 80 μm to 200 μm, preferably is equal to 142 μm.

In a further embodiment, the mesh portion is convex such as to follow the eye curvature.

These dimensions are small enough to reduce the impact of the device into the eye while maintaining the functionality of the drainage.

In a further embodiment, the connection portion has a substantially truncated cone shape with a portion having the greatest width and smallest height at the mesh portion.

In a further embodiment, the glaucoma implant device comprises a stent portion coupled to the connection portion,
  wherein the stent portion is able to dilate the Schlemm canal and to direct aqueous humour from Schlemm canal to collectors channels and to the connection portion, and
  wherein the connection portion has a substantially truncated cone shape with a portion having the smallest width and greatest height at the stent portion, wherein said greatest height is equal to the height of said stent portion.

In a further embodiment, the stent portion is defined by an elongated element curved according to the radius of the Schlemm Canal,
  wherein the outer surface of the stent portion is provided with a plurality of apertures defining a void area of the outer surface, wherein the void area is greater than the solid area of the outer surface, and
  wherein the inner portion of the stent portion is provided with a stiffening structure in contact with the inner portion of the outer surface and defining a solid volume of the inner portion, wherein the inner portion has the void volume greater than the solid volume.

In a further embodiment, the stent portion ranges from 3 mm to 8 mm in length, preferably is 5 mm in length, and
  wherein the stent portion has an ellipsoid cross shape having a major axis ranging from 200 μm to 400 μm, preferably from 280 μm to 350 μm, and a minor axis ranging from 50 μm to 150 μm, preferably from 80 μm to 122 μm.

In a further embodiment, the stent portion and/or said connecting portion are provided with a plurality of hollow microneedles on the outer surface facing said trabecular meshwork,
  wherein the dimension in height of the hollow microneedles ranges from 20 μm to 40 μm, preferably is 25 μm.

The microneedles are able to ensure hydraulic patency from the tip of the microneedles to the internal part of the stent portion and of the connection portion.

DESCRIPTION OF THE FIGURES

These and further features and advantages of the present invention will become apparent from the disclosure of the preferred embodiment, illustrated by way of non-limiting example in the appended drawings, wherein.

DETAILED DESCRIPTION OF THE INVENTION

With reference to FIGS. 1 to 10 and FIG. 11, a first preferred embodiment and a second embodiment of the glaucoma implant devices 1, according to the present invention, are illustrated. In the present invention, the numbering of identical parts will be kept the same through the different embodiments.

Figure 1:
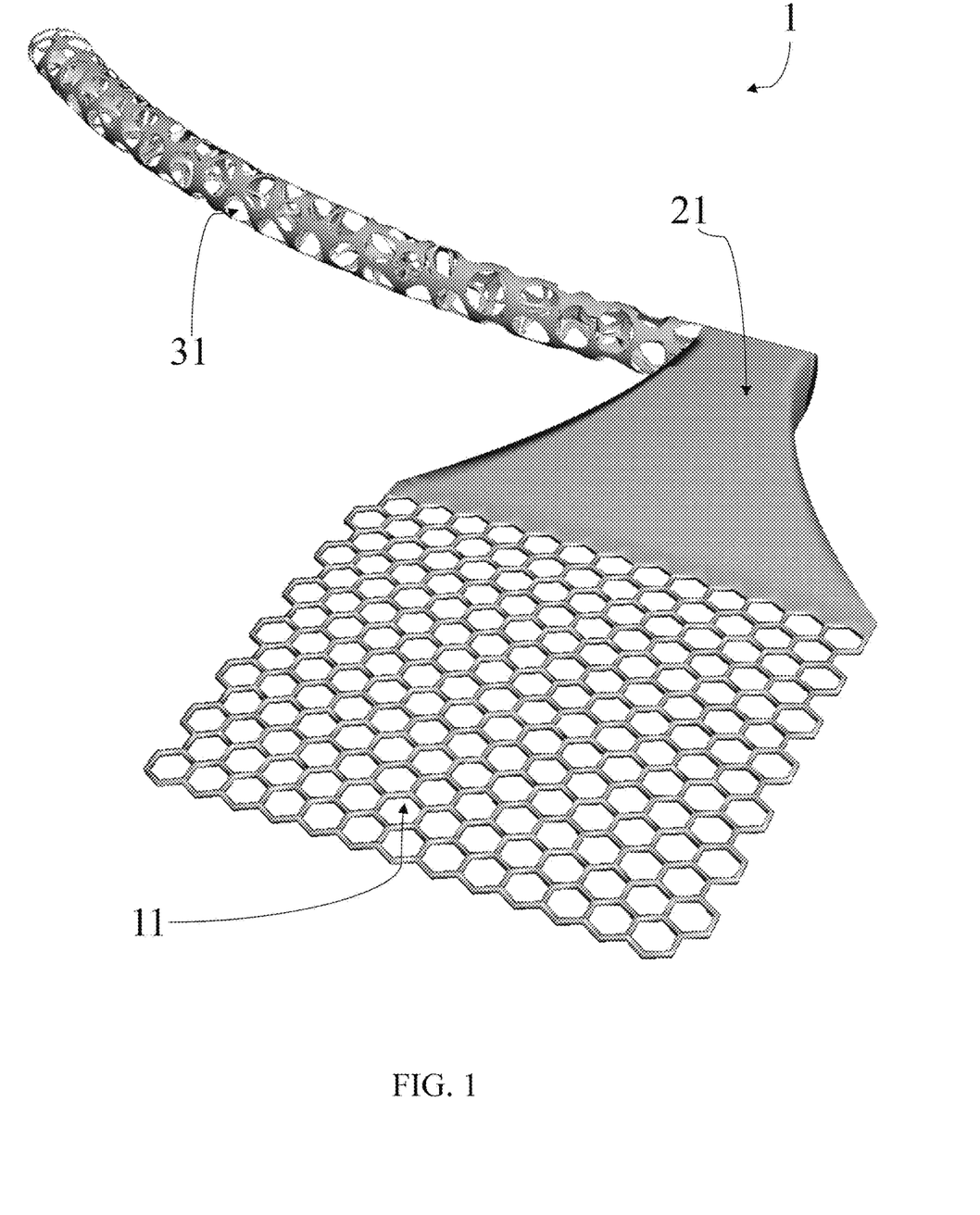
FIG. 1 is a prospective top view of the first preferred embodiment of the glaucoma implant device, according to the present invention.
Figure 2:
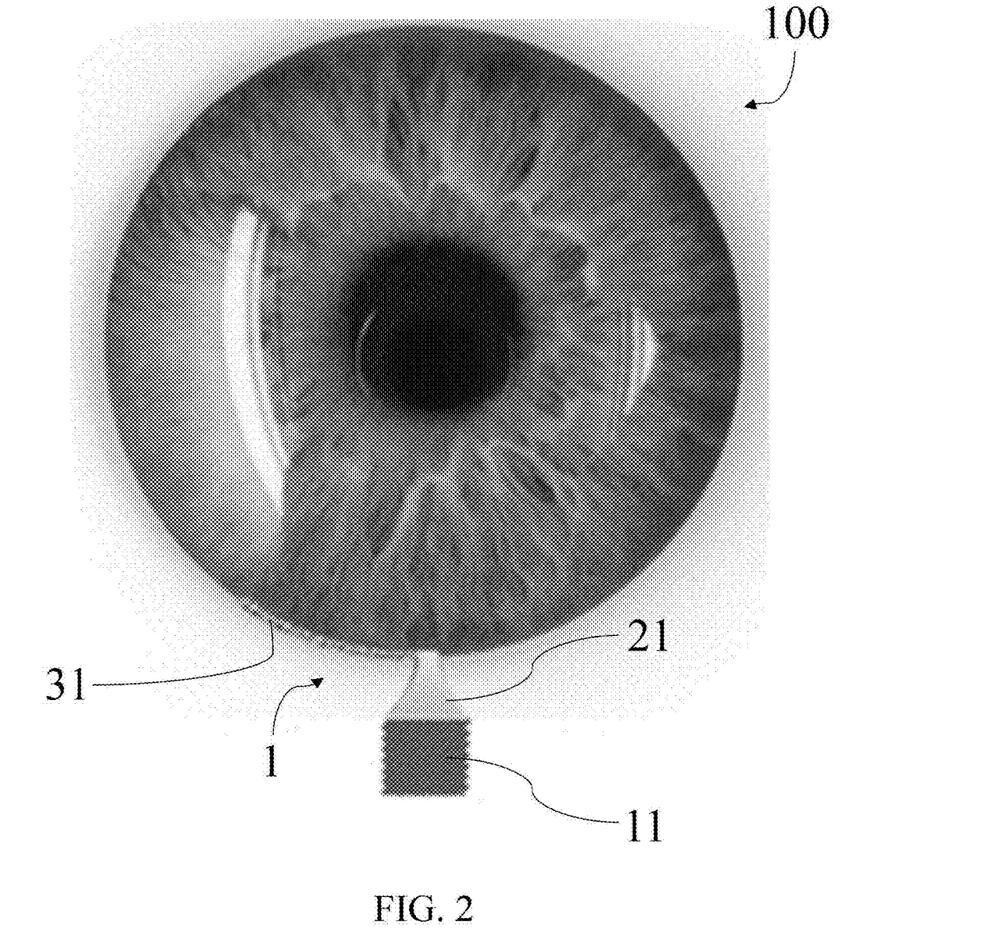
FIG. 2 is a schematic front view of the glaucoma implant device of FIG. 1 when implanted in the eye to be treated.

With reference to the first preferred embodiment, FIG. 1 illustrates a prospective top view of the glaucoma implant device 1, according to the present invention. The same glaucoma implant device 1 is illustrated in FIG. 2 in a schematic implantation into the eye 100 to be treated.

As illustrated, the glaucoma implant device 1 of the first embodiment comprises a mesh portion 11, a connection portion 21 and a stent portion 31. The mesh portion 11 is coupled to the connection portion 21. Moreover, the connection portion 21 is coupled to the stent portion 31. In present demonstrated configuration stent portion 31 is connected to the left of connection portion 21, but it can equally be connected to the right of connection portion. The interconnected portions of the device 1 are preferably made of solid biocompatible polymer, which will be described in greater details in the following.

According to further embodiments, not illustrated, the glaucoma implant device may comprise only one of the aforementioned portions or a combination or two of the aforementioned portions, such as the mesh portion and the connection portion.

The stent portion 31 is able to dilate the Schlemm canal and to direct aqueous humour from Schlemm canal to the connection portion 21 and facilitate its drainage into collector channels at the same time. In turn, the connection portion 21 is able to direct aqueous humour from Schlemm canal and anterior chamber directly via micro needles array to the mesh portion 11 and the mesh portion 11 is able to drain aqueous humour into subconjunctival or suprachoroidal space when the glaucoma implant device 1 is implanted.

The aqueous humour is a transparent water-like fluid similar to plasma, but containing low protein concentrations. It is secreted from the ciliary body, a structure above the lens and flows through anterior chamber, providing nutrition to the eye and maintaining the eye 100 in a pressurized state.

Aqueous humour is continually produced by the ciliary processes and this rate of production must be balanced by an equal rate of aqueous humour drainage. Small variations in the production or outflow of aqueous humour will have a large influence on the intraocular pressure. Normally the production rate is more or less steady; therefore TOP management mostly focuses on outflow facilitation.

The drainage route for aqueous humour flow is first through the posterior chamber, then the narrow space between the posterior iris and the anterior lens, through the pupil to enter the anterior chamber. From there, the aqueous humour exits the eye through the trabecular meshwork into Schlemm's canal (a channel at the limbus, i.e., the joining point of the cornea and sclera, which encircles the cornea). The greatest resistance to aqueous flow is provided by the trabecular meshwork (especially the juxtacanalicular part), and this is also where most of the aqueous outflow occurs. The internal wall of the Schlemm's canal is very delicate and allows the fluid to filter due to high pressure of the fluid within the eye. The secondary route is the uveoscleral drainage, and is mostly independent of the intraocular pressure, the aqueous flows through here, but to a lesser extent than through the trabecular meshwork (approximately 10% to 50% of the total drainage depending on age and other factors, whereas by trabecular meshwork 90% or less of the total drainage).

The eye pressure, occurring due to constant delicate balance between aqueous humour production and outflow is normally in the range of 12-22 mm Hg. IOP above 22 mm Hg is considered higher than normal and might require control.

Glaucoma is a progressive optic neuropathy where retinal ganglion cells and their axons die causing a corresponding visual field defect. An important risk factor is increased intraocular pressure (pressure within the eye) either through increased production or decreased outflow of aqueous humour. Increased resistance to outflow of aqueous humour may occur due to an abnormal trabecular meshwork or due to obliteration of the meshwork resulting from injury or disease of the iris. Uncontrolled glaucoma typically leads to visual field loss and ultimately blindness. There is no cure or reverse for glaucoma. The therapy is focused to the control of further progression of this chronic condition via reducing and controlling internal eye pressure.

The glaucoma implant device 1, according to the present invention, that one or more of its portions, allows for the management and better control of the aqueous humour outflow, in particular important to the management of the glaucoma neuropathy.

Figure 3:
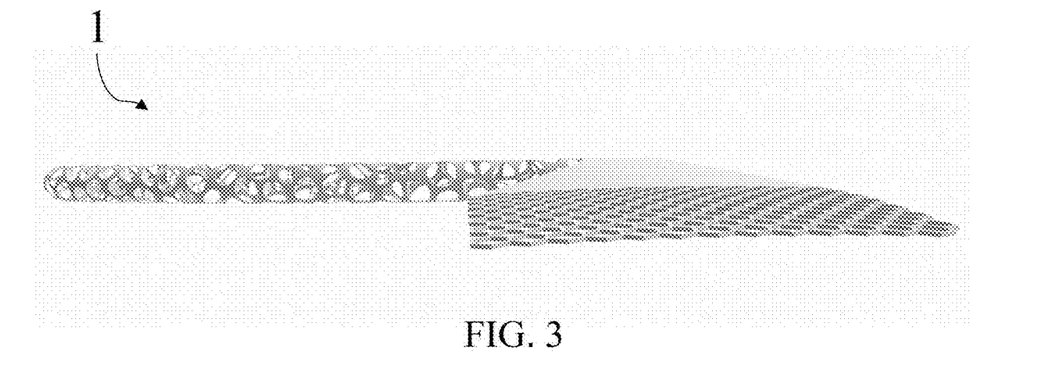
FIG. 3 is a is a prospective lateral view of the glaucoma implant device of FIG. 1.

FIG. 3 illustrates a prospective lateral view of the glaucoma implant device 1 of FIG. 1, wherein the small dimension in height of the overall device 1 can be appreciated.

Figure 4:
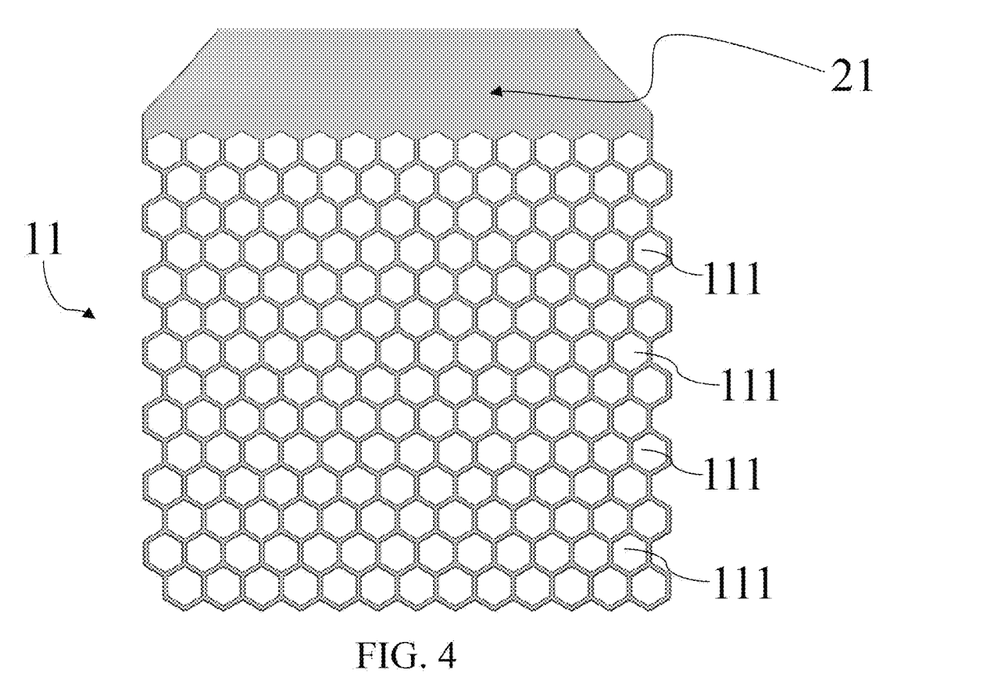
FIG. 4 is a schematic top view of a detail of the glaucoma implant device of FIG. 1, relating to the mesh portion.

The mesh portion 11 of the glaucoma implant device 1 is illustrated in greater detail in FIG. 4, wherein it is represented in a schematic top view. Such a mesh portion 11 is defined by a plurality of polygonal cells 111 arranged side-by-side in contact to each other according to a predefined number of rows and columns.

In the illustrated embodiment, the mesh portion 11 consists of a plurality of 182 cells defined by a number of rows equal to 14 and a number of columns equal to 13. The number of cells may vary according to different embodiment and, for example, the predefined number of rows may range from 10 to 20 while the predefined number of columns may range from 10 to 20.

Figure 6:
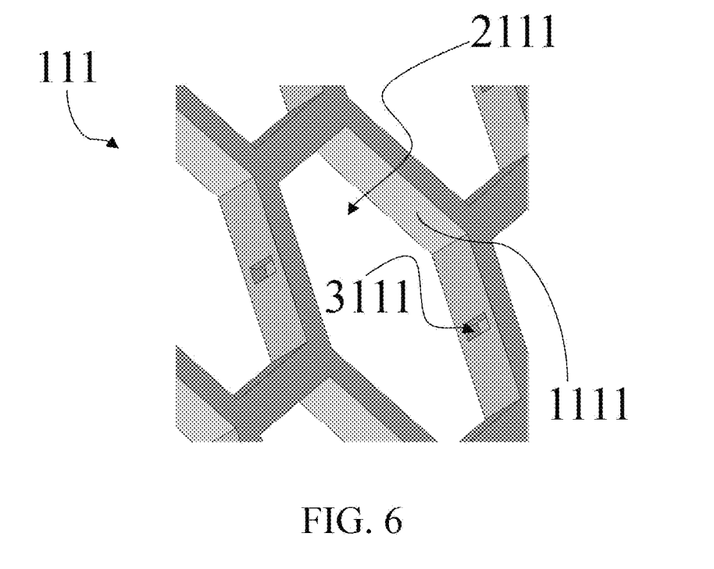
FIG. 6 is a schematic prospective view of a detail of the mesh portion of FIG. 4, relating to the polygonal cells at the last hexagon row of the mesh.

Details about the polygonal cell 111 are illustrated in FIG. 6. In particular, each of the polygonal cells 111 has perimetral sides 1111 and a through opening in-between defining a liquid collecting area 2111. Moreover, each of the polygonal cells 111 is provided with at least an opening 3111 at the perimetral side 1111.

Figure 7:
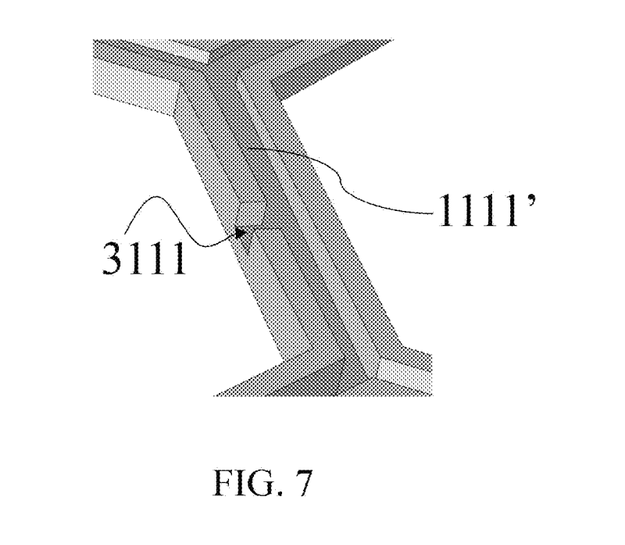
FIG. 7 is a schematic cross section prospective view of a portion of the polygonal cells of FIG. 6, relating to the inner duct at the last hexagon row of the mesh.

FIG. 7 illustrates a cross section in enlarged view of the polygonal cell 111 of FIG. 6. Apart from the aforementioned opening 3111, in FIG. 7 an inner duct 1111' can be seen, such a duct being defined by the same perimetral side 1111 already described.

Preferably, all perimetral sides are provided with said inner duct but in a further embodiment, not illustrated, it is still possible to have inner ducts only in a portion of said perimetral sides.

Anyway, the inner ducts 1111' are in hydraulic connection to each other and, in particular, with the respective openings 3111 (or the openings 3111 in the respective polygonal cell 111). In this way, the openings 3111 are able to connect the inner ducts 1111' to the liquid collecting area 2111 via outlet ducts 112 allowing the draining of aqueous humour into subconjunctival or suprachoroidal space by flowing out from the inner ducts 1111' to the liquid collecting areas 2111.

In turn, one or more of the inner ducts 1111' are in hydraulic connection with the connection portion 21, as illustrated in FIG. 4, allowing the directing of aqueous humour from Schlemm canal to the mesh portion.

Therefore, the mesh portion 11 defines a microfluidic matrix, through which aqueous humour drains into subconjunctival or subchoroidal space.

In the mesh portion 11 according to the first embodiment, the structure of the cells 111 is of the hexagon shape devoid of basis such as to define the through opening in-between and, in turn, the liquid collecting area 2111. According to further embodiments, not illustrated, the shape of the cells may vary within a polygonal choice.

The openings 3111, therefore, define fluid outlet ducts 112 designed to act as built in pressure resistors, formed by mathematically defined diameter and length. This will result, for example, in built-in hypotony prevention tool, not allowing for TOP drop below 5 mmHg anytime, making life of surgeons easier. More precisely, via parametrization of the outlet ducts 112, the pressure resistance in the mesh portion 11 is regulated as to desired flow rate. Moreover, all the outflow through the mesh portion 11 happening at the same rate and same time across all the liquid collecting areas 2111 of the mesh portion 11. This would mean that there is no usual, random bleb (as no resistance is needed nor little is happening at the point of contact with conjunctiva), and almost no pressure to surrounding tissues—the aqueous simply passively diffuse into surrounding capillaries from 2111. Given that good functioning bleb measurements statistically are about 3 mm±2.2 mm×2.72 mm±2.02 mm, the mesh portion 11 should have similar surface area, but potentially better characteristics as these of the bleb (for example, no visible bleb for cosmetic purposes, potentially less infections, potentially less fibrotic reaction due to minimized foreign material exposure to the body, potentially standardized outflow resistance outcome bringing personalized medicine one step closer). Mesh portion 11 itself resembles highly organized standardized microcysts, a feature of well-functioning bleb.

Therefore, preferably, the mesh portion 11 has a dimension ranging from 1 mm in length and 1 mm in width to 4 mm in length and 4 mm in width, more preferably is 2 mm in length and 2 mm in width. Moreover, preferably, the mesh portion 11 has a dimension ranging from 101 µm to 501 µm in height, more preferably is 201 µm in height. Furthermore, preferably, the perimetral sides 1111 have a dimension ranging from 151 µm to 401 µm in width, more preferably is 201 µm in width. Consequently, preferably, the diameter of the main inner ducts 1111' ranges from 5 µm to 12 µm, more preferably is equal to 8 µm. Accordingly, preferably, the dimension of the openings 3111 ranges from 4 µm to 10 µm, more preferably from 5 µm to 8 µm. Accordingly, the dimensions of the outlet ducts 112 are differentiated and mathematically modeled according to finite elements analysis as to achieve desired pressure resistance threshold while leaking aqueous humor through the whole mesh portion 11 area simultaneously.

These dimensions are small enough to reduce the impact of the device into the eye while maintaining the functionality of the drainage.

Moreover, taking into account the hexagon shape of the cells 111, the mesh portion 11 has a hexagon periodicity ranging from 80 µm to 200 µm, preferably is equal to 142 µm.

Even if not shown, mesh portion 11 might have, in case of need, embedded non-functional solid design elements providing mechanical support and reinforcing stability to such a mesh portion 11.

In consideration of the insertion of the mesh portion 11 in the eye, the mesh portion 11 is convex, i.e. slightly convex, such as to follow the eye curvature. For example, the convexity may be defined by a circular segment angle of 9.5493° and arc height of 41.64 µm. By having mesh portion 11 following curvature of the eyeball, we remove any potential excessive effects on surrounding tissues due to implant form adaptation to it and elasticity of material which might induce stronger foreign body reaction at the points of higher implant pressure to tissues.

The structure of the mesh portion 11 resembles large flat pseudo openings and should result in significant reduction of fibrotic response. On the other hand, some research has demonstrated that micromesh induces very little fibrotic reaction compared with the plate models. Therefore, it is a scope of the present invention to make design choices seek to minimize material footprint in the eye.

In this regard, having openings ranging from 41 µm to 10 µm, more preferably from 51 µm to 8 µm should also prevent cells and macrophages colonization of inner ducts 1111'. The size of corneal cells varies but a superficial cell can be 50 µm in diameter and 51 µm in height. Myofibroblasts are relatively elongated cells, about 20-30 µm long. Therefore, inner ducts 1111' of 81 µm or even of 41 µm should be considered as good enough in prevention of cellular ingress into them in absence of strong flow.

The negative hydrostatic pressure gradient between anterior chamber and anterior suprachoroidal (at limbus) space is 0.8 mmHg, and increases going towards back of the eye, reaching 3-4 mmHg between anterior chamber and posterior suprachoroidal space that provides a driving force for aqueous humour outflow here. To obtain very low TOP via suprachoroidal placement, there is a need to overcome ciliary muscle which is about 2192.1 µm±261.8 µm long. Therefore, it is possible to couple each other the mesh portion 11 with the connection portion 21 in order to achieve proper location of the mesh in regards of suprachoroidal placement, shall suprachoroidal space be the choice of surgeons. Preferably, the coupling of the selected measurements is such that the mesh portion 11 is located at least 2 mm below limbus. This corresponds also with the current state of art surgery procedures of suprachoroidal space.

The connection portion 21 directs aqueous humour from Schlemm canal to microfluidic mesh portion 11. Being more sturdy than other parts of the implant, it also is the main touch point for manipulation during surgery, to withstand light manipulation with forceps, extraction of stent if needed and for contact with pushing elements of injector (if any).

Preferably, the connection portion 21 has a substantially truncated cone shape, as illustrated in FIGS. 1-4, with a portion having the greatest width and smallest height at the mesh portion 11, and with horizontal curvature shaped as to fit for subscleral or suprachoroidal placing when requested. The latter is better illustrated in FIGS. 1 and 3, and specifically in FIG. 4.

Figure 8:
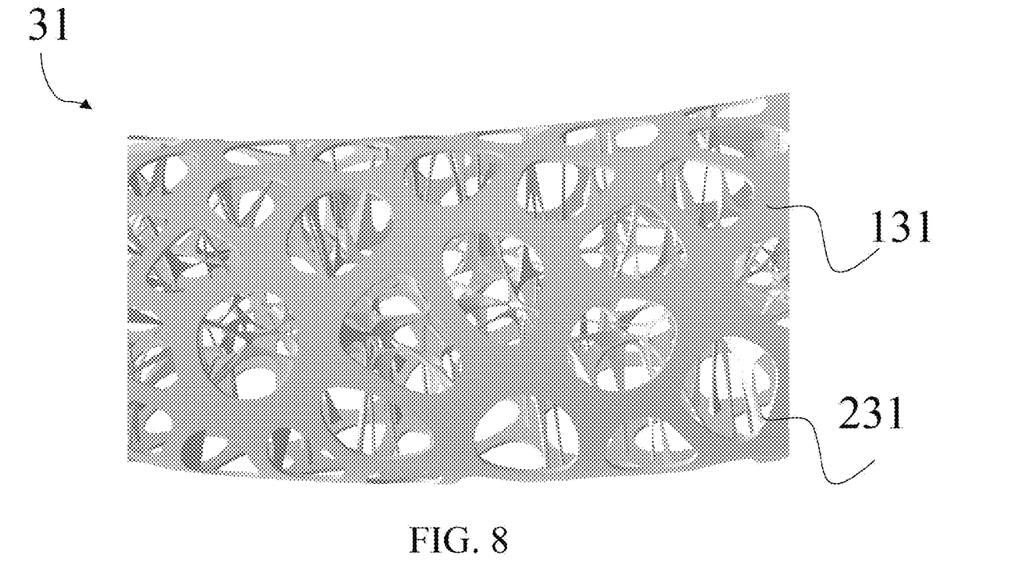
FIG. 8 is a schematic perspective front view of a detail of the glaucoma implant device of FIG. 1, relating to the stent portion.
Figure 9:
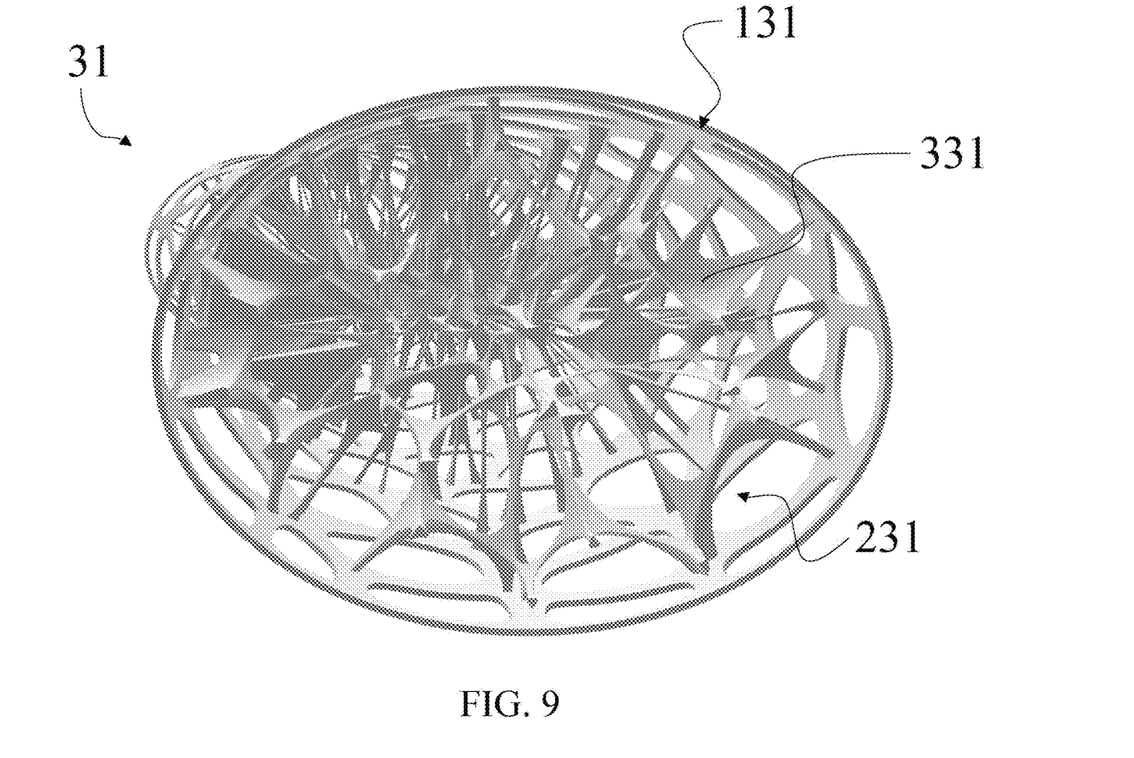
FIG. 9 is a schematic perspective lateral view of the stent portion of FIG. 8.
Figure 10:
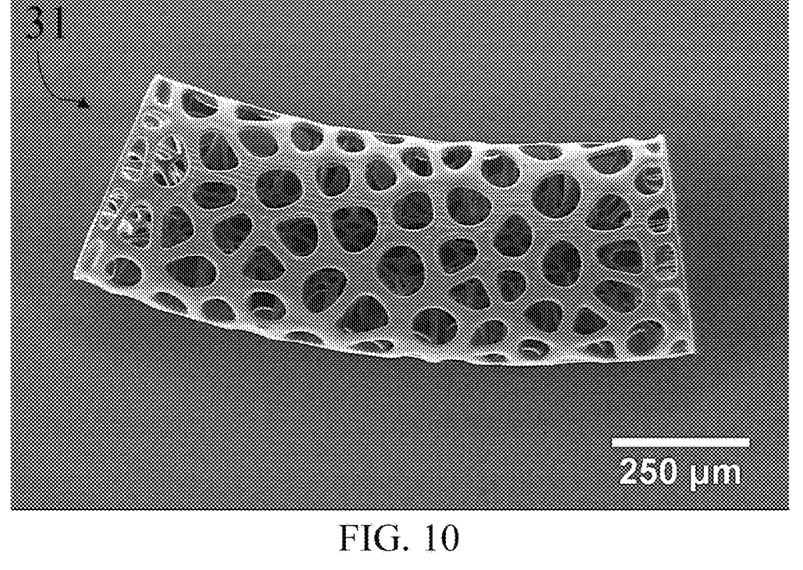
FIG. 10 is a perspective top view of the part of stent portion of FIG. 8, in micrometric scale comparison in real life.

Finally, FIGS. 8-10 illustrate a perspective view of the stent portion 31 of the glaucoma implant device 1, according to the present invention. The scope of the stent portion 31 is to dilate the Schlemm Canal and is coupled (eventually) with the aforementioned connection portion 21 from left or the right side to it as needed.

When the glaucoma implant device 1 comprise all the three portions already described, such a connection portion 21 has a substantially truncated cone shape with a portion having the smallest width and greatest height at the stent portion 31, thus being completely different to the design at the mesh portion 11. More precisely, the height and width of the connection portion 21 at the stent portion 31 is equal to the height and width of the stent portion 31 (more precisely, diameter and cross section at the coupling side being the same of connection portion 21 and stent portion 31), while its width (or the length of connection portion 21 being placed into Schlemm canal) being from 200 µm to 1,000 µm, but preferably 500 µm.

The stent portion 31 is defined by an elongated element curved, i.e. anatomically curved, according to the radius of the Schlemm Canal and having preferably an ellipsoid cross shape, i.e. having an oval shape according to the Schlemm Canal, but different shapes may be used according to further embodiments (not illustrated). Such a curvature preferably corresponds to 30 to 70 degrees but preferably 48 degrees of 12.0957 mm diameter circle.

When cut in cross section, the Schlemm Canal has the appearance of a highly elongated ellipse, with its major axis having a diameter varying between 150 µm and 3501 µm (250-280 µm average); while the minor axis can vary between roughly 11 µm and 301 µm, depending on the IOP. Stent portion 31 is designed as to achieve dilation targets of about 25% over median Schlemm Canal measurements, therefore it does not over dilate and does not excessively damage naïve tissues of Schlemm Canal.

Therefore, according to the preferred embodiments, the stent portion 31 ranges from 3 mm to 8 mm in length, preferably is 5 mm in length including coupling part with connecting part 21 corresponding to the smallest width of the connection portion. Moreover, the ellipsoid cross shape has a major axis ranging from 200 µm to 400 µm, preferably from 280 µm to 350 µm, and a minor axis ranging from 50 µm to 150 µm, preferably from 80 µm to 122 µm. By taking nominal values of Schlemm Canal 2801 µm and 301 µm, the applicant has arrived at the calculated measurements of the ellipse with major axis in the range of 280-350 µm and minor axis in the range of 80-122 µm. In this regard, FIG. 10 is a perspective top view real life picture of the element of the stent portion 31 in micrometric scale comparison.

The length of the stent portion 31 including coupling part with connecting part 21 is 2 to 3 hours (between 8 and 4 millimeters, most probably 5 millimeters) to potentially reach at least two Collection channels. It is known that the length of Schlemm Canal between two Collection Cannels is about 1.2 mm. It is known that only a portion, perhaps a third, of the trabecular outflow pathway is active in fluid passage at any one time and it is not yet possible to target Collector Channels, but length of the implant should increase the chance of success. The design of implant 1 is such that the success of procedure would be less dependent on successfully finding and targeting collector channels. This is possible because of exploitation of both conventional and non-conventional aqueous drainage routes in the same implant device, while failure of one route shall be amortized by increase of drainage on the other route, particularly via mesh portion 11.

The outer surface 131 of the stent portion 31 is provided with a plurality of apertures 231 defining a void area of the outer surface 131, wherein the void area is greater than the solid area of the same outer surface 131

Moreover, the inner portion of the stent portion 31 is provided with a stiffening structure 331 in contact with the inner portion of the outer surface 131 and defining a solid volume of the inner portion, wherein the inner portion has the void volume greater than the solid volume.

Therefore, the stent portion 31 has minimal surface geometry (such as based on Voronoi or gyroid type patterns) which remains sturdy enough but minimizes foreign body footprint (and potentially inflammatory processes) in the eye while allowing almost completely free flow within itself, minimizing potential of occlusion of orifices of collector channels. In the case if the microneedles array as described below is used to microperforate juxtacanicular tissue to restore patency from the anterior chamber into Schlemm canal, such a design would ensure unrestricted flow from anterior chamber into collector channels while preserving remaining functionality and structures of trabecular meshwork.

Preferably, even if not illustrated, the free end of the stent portion 31 has a rounded dome design, i.e. rounded conical end shape, for easier insertion into Schlemm Canal. The opposite end of the stent portion 31, instead, being coupled with the connection portion 21.

In a further embodiment, not illustrated, the stent portion may be provided with a continuous central column arranged in the middle axis of inner portion, to improve crushing resistance of the same stent portion during insertion into Schlemm Canal. Such a continuous solid central column may have a diameter ab out 20 µm.

In a further embodiment, the stent portion may comprise a barrier, i.e. a vertical barrier, to internally separate or partly separate the inner space of coupling with the connection portion, thus separating Schlemm canal and uveoscleral filtration routes. Such a barrier may preferably be positioned between 500 µm to 2,000 µm but most probably at 750 µm from the non-stent portion side of connection portion 21.

Figure 12:
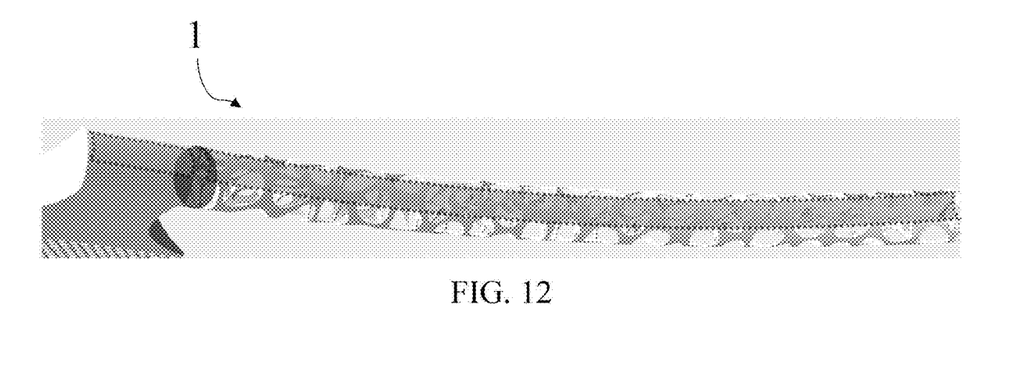
FIG. 12 is a prospective rear view of the glaucoma implant device, according to the present invention.
Figure 13:
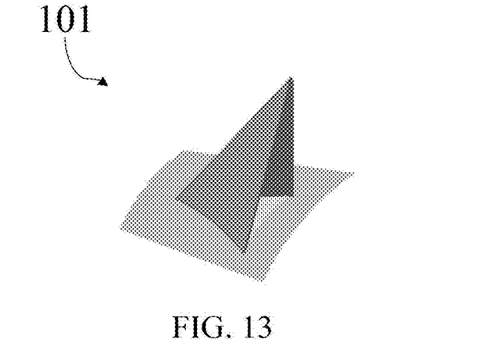
FIG. 13 is a prospective front view of a hollow microneedle in a first embodiment, according to the present invention.
Figure 14:
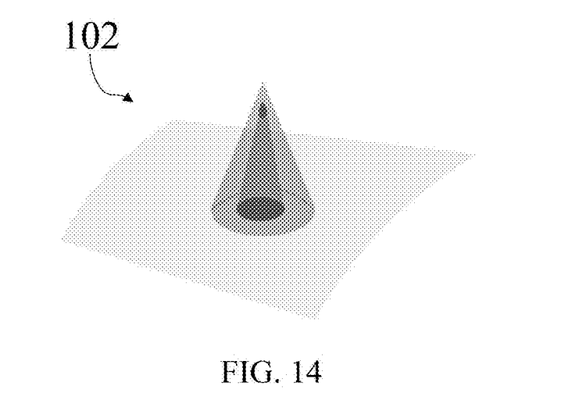
FIG. 14 is a prospective front view of a hollow microneedle in a second embodiment, according to the present invention.

While only the dilation of Schlemm canal improves its patency and protects from collapse, it is possible to improve further the drainage with the stent portion. In this regard, in a further embodiment, the area of the stent portion 31 and connection portion 21 side facing trabecular meshwork may be or may be not provided with a plurality of hollow microneedles on the outer surface, as illustrated in FIGS. 13 and 14 according to two different embodiments, defining therefore a plurality of additional ducts. More precisely, such micro needles array might be present on stent portion 31, on connection portion 21, or both as illustrated in the dotted portion of FIG. 12, or none.

It is well known that the major site of resistance resides in the juxtacanalicular portion of trabecular meshwork within 7-14 µm of the inner wall of Schlemm Canal. Juxtacanalicular tissue itself has pores of diameters of up to 11 µm and measures in 2-20 µm thickness. Given a short length (thickness), a single 12 µm hole in trabecular meshwork would be sufficient to ensure normal aqueous humour outflow. Therefore stent portion may be provided with a self-perforating microneedles array mimicking single pores. The number of pores shall be between 30-100, but most probably 50. In any case it will create surplus patency ensuring restored porosity and almost unhindered outflow from the anterior chamber to Schlemm canal. Microneedles will ensure least aggressive intervention into trabecular meshwork and will retain its remaining natural filtering function and phagocyte activity, allowing filtered aqueous flow into Schlemm canal and later into uveoscleral space. This is a significant difference from other approaches having relatively large (several tens or hundreds of µm) openings penetrating trabecular meshwork completely with exit into anterior chamber. Another advantage of such quasi-perforation might be reduced risk of endothelial cell loss. As recent data with some implants protruding into the anterior chamber shows, not only contact with cornea, but even proximity to it results in accelerated endothelial cell loss, a major problem. With the present invention the patency will be restored, but with main layers of Trabecular meshwork left intact. Some other Schlemm Canal implants have issues in regards to the potential harm to adjacent tissue caused by relatively high fluid flow rates at or around any portion of the device. In our case the flow would be distributed along the stent portion.

The dimension in height of the hollow microneedles may range from 20 µm to 40 µm, preferably is 25 µm. Moreover, the dimension of the ducts defined by the aforementioned microneedles ranges from 3 µm to 6 µm, preferably is 4 µm and the microneedles themselves have submicron sharpness tip.

The microneedles may also have a conical or tetrahedron pyramid shape, in the latter one side wall being removed and other walls being isosceles triangles with base angle of 50° to 80° degrees but preferably is 72°.

The microneedles array may also extend on the connecting portion 21 of the implant.

Therefore, the microneedles are able to ensure hydraulic patency from the orifice at the tip of the microneedles to the internal part of the stent portion 31.

In case if the microneedles are not used, the connection portion may have a single opening into the Anterior chamber, in which case it may have a built-in filter to prevent debris or blood clot getting into Schlemm canal. The connection portion may also be shaped to adapt to anatomical features of the eye depending on the subscleral or suprachoroidal position of the implant so that when the stent portion 31 together with ending part of the connection portion 21 is inserted into Schlemm Canal, the connecting part of the connection portion with the mesh portion 11 lays in its desired position without uprooting force.

Figure 5:
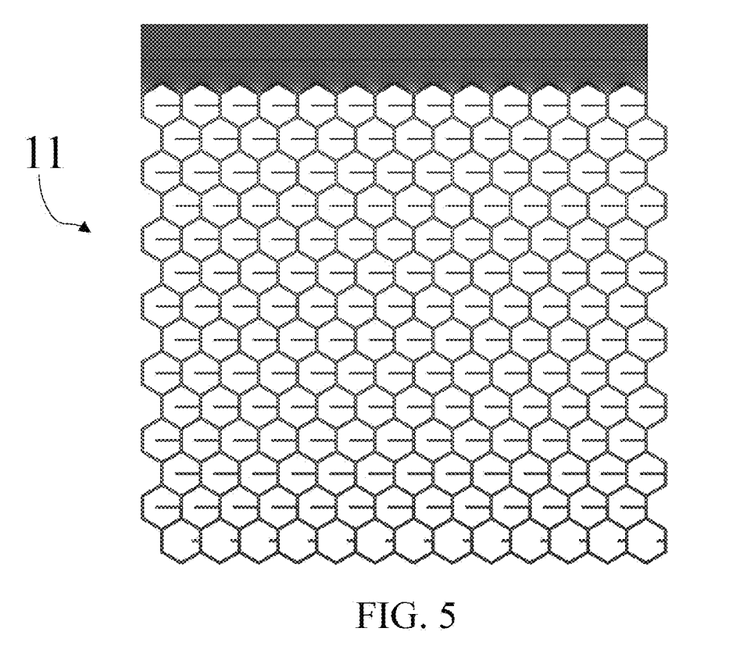
FIG. 5 is a schematic top view of the internal ducts of the mesh portion of FIG. 4 during drainage with 901 degrees layout.
Figure 11:
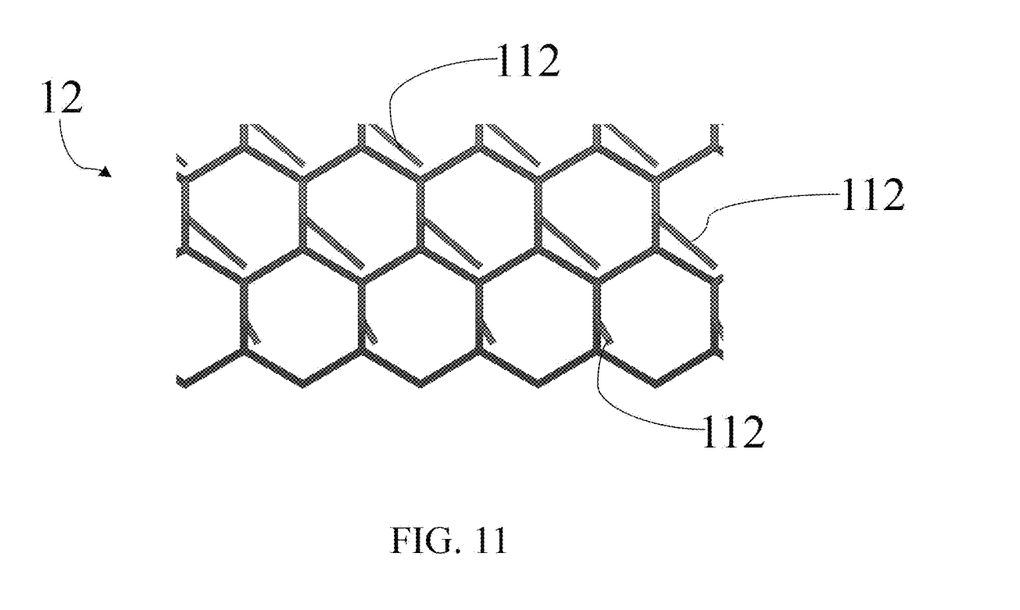
FIG. 11 is a schematic front view of a detail of the glaucoma implant device according to a second embodiment, relating to the mesh portion.

FIG. 5 is a schematic top view of the inner ducts 1111' and openings 3111 in the mesh portion of FIG. 4 during drainage. It is evident that differences in pressure and in the drainage in the liquid collection areas shall occur due to different parameters of outlet ducts 112 and openings 3111. Therefore, FIG. 11 is a schematic front view of a detail of the glaucoma implant device according to a second embodiment, relating to the mesh portion 12, wherein each of the polygonal cells is provided with an outlet duct 112 departing from the opening and extending in the same liquid collecting area. More precisely, outlet ducts 112 are inseparable and end with openings 3111.

As illustrated, the outlet ducts 112 may have different inclinations ranging from 15° to 90° with respect to the perimetral side provided with the opening. Moreover, the outlet ducts 112 shall have different lengths and diameters such that to achieve a predefined hydraulic resistance threshold of the mesh portion allowing the draining of aqueous humour into subconjunctival or suprachoroidal space by flowing out from the inner ducts to the respective liquid collecting areas simultaneously.

The parameters of the outlet ducts 112 are modeled mathematically as to achieve desired hydraulic resistance threshold of the mesh portion as a whole and to let aqueous outflow via the whole area of the mesh portion to be done simultaneously.

In a further embodiment, the outlet ducts have a dimension ranging from 2 µm to 20 µm in diameter, preferably from 4 µm to 15 µm, and ranging from 15 µm to 100 µm in length.

The glaucoma implant device 1 according to the present invention may be produced by additive manufacturing. Additive technology may be used, for example, for manufacturing a glaucoma implant device, according to the present invention, which allows a selection of different diameters and mixed elements of the implant device 1 to correspond to individual needs of the patients.

Preferably, the glaucoma implant device 1 is made of a biocompatible photoresist material, more preferably by a hybrid organic-inorganic 20/80 zirconium-silicon acrylate sol-gel. Alternatively, other suitable biocompatible photoresist materials might be used if fit for the purpose.

In the latter case, the glaucoma implant device 1 may be obtained by a process comprising the following phases:
producing a structure of the glaucoma implant device 1 by irradiating with a femtosecond laser the hybrid organic-inorganic 20/80 zirconium-silicon acrylate sol-gel, wherein the structure has the same shape and dimension as the final structure of the glaucoma implant device 1;
obtained structure is subsequently submerged into an organic solvent, such as 2-propanol, acetone or Isobutyl Methyl ketone. This removes laser unaffected volume, revealing produced structure. Drying after development can be performed either in ambient atmosphere or in critical point dryer (CPD). Structure is ready to use after drying. If needed it can also be disinfected using standard organic disinfectants or other industry standard sterilization methods.

The glaucoma implant device according to the present invention therefore provides to significantly reduce the fibrotic encapsulation, while maintaining the direction of aqueous humour.

The invention aims also to exploit additive micromanufacturing technology possibilities and freedom to device geometry to advance glaucoma implants effectiveness and overcome some obstacles present so far by the state of art devices.

The glaucoma implant device according to the present invention dilates Schlemm canal and provides access to uveoscleral outflow route simultaneously, therefore overcoming TOP floor in Schlemm canal. The stent portion is designed to use minimal surface geometry (such as gyroid) to retain structural strength but also to minimize foreign material footprint in Schlemm canal. The length of the stent portion is to cover at least the distance between two collection channels. Minimal surface geometry minimizes chances to occlude collection channels and at the same time minimizes contact with surrounding cells.

Eventually, the stent portion micro-perforates juxtacanalicular connective tissue of trabecular meshwork in multiple points to restore patency from anterior chamber into Schlemm canal via trabecular meshwork. Since corneoscleral meshwork and uveal meshwork remain intact, the penetration is conditional, and the remaining filtering function of trabecular meshwork stays intact.

The stent portion may also be connected to several square millimeters of mesh portion, distanced from Schlemm canal by several millimeters, thus reaching pars plana where aqueous absorption is better if suprachoroidal placement is chosen or positioned subsclerally again below Schlemm canal. The mesh portion may be geometrically convex to follow eyeball curvature and positioned in subscleral space.

The stent portion may also be separated from the meshwork part by a vertically positioned internal barrier at connecting portion. Such a choice might be dictated by the need to obtain very low internal pressure levels in which case there is a small chance of reflux from episcleral veins into meshwork part and even anterior chamber and by the need for more precise internal pressure control at meshwork level.

Finally, mesh portion is modelled so that all the surface is draining at equal rate (therefore effectively replacing bleb without bleb related problems) and the mesh portion itself is acting as a mathematically modelled aqueous resistor not allowing hypotony of at any time. Since the pressure resistance is confined in the mesh portion at a certain threshold by its design, there is no such pressure to surrounding tissues which normally is inducing stronger fibrotic reaction as in currently used implants.

The invention claimed is:

1. A glaucoma implant device (1) comprising a connection portion (21) and a mesh portion (11) coupled to each other,
   wherein said connection portion (21) is able to direct aqueous humour from Schlemm canal and anterior chamber to said mesh portion (11) and said mesh portion (11) is able to drain aqueous humour into subconjunctival or suprachoroidal space when said glaucoma implant device (1) is implanted,
   wherein said mesh portion (11) is defined by a plurality of polygonal cells (111) arranged side-by-side in contact to each other according to a predefined number of rows and a predefined number of columns,
   wherein each of said polygonal cells (111) has perimetral sides (1111) and a through opening in-between defining a liquid collecting area (2111),
   wherein each of said perimetral sides (1111) defines an inner duct (1111'), said inner ducts (1111') being in hydraulic connection to each other,
   wherein one or more of said inner ducts (1111') are in hydraulic connection with said connection portion (21) allowing said directing aqueous humour from Schlemm canal to said mesh portion (11), and
   wherein each of said polygonal cells (111) is provided with at least an opening (3111) at a perimetral side (1111) able to connect said inner duct to said liquid collecting area (2111) allowing said draining of aqueous humour into subconjunctival or suprachoroidal space by flowing out from said inner ducts to said liquid collecting areas (2111); wherein each of said polygonal cell (111) is provided with an outlet duct (112) departing from said inner duct (1111') and ending with said opening (3111) and extending in said liquid collecting area (2111), and wherein said plurality of polygonal cells (111) includes:
   a first group of polygonal cells provided with a first group of said outlet ducts having a first length and a first diameter; and at least a second group of polygonal cells provided with a second group of said outlet ducts having a second length different from said first length and a second diameter different from said first diameter;
   wherein, said first group of outlet ducts and second group of outlet ducts are configured such that said mesh portion (11) has a predefined hydraulic resistance threshold whereby the first length is greater than the second length and the first group of polygonal cells is nearer to the connection portion (21) than the second group of polygonal cells.

2. The glaucoma implant device (1) according to claim 1, wherein said outlet ducts (112) have a different inclination ranging from 15° to 90° with respect to said perimetral side (1111) provided with said opening (3111), and
   wherein said first group of outlet ducts and second group of outlet ducts are configured such as that said draining of aqueous humour into subconjunctival or suprachoroidal space by flowing out from said inner ducts to said respective liquid collecting areas (2111) is simultaneous.

3. The glaucoma implant device (1) according to claim 2, wherein said outlet ducts (112) have a diameter ranging from 2 μm to 20 μm.

4. The glaucoma implant device (1) according to claim 1, wherein said mesh portion (11) has a length and width ranging from 1 mm in length and 1 mm in width to 4 mm in length and 4 mm in width.

5. The glaucoma implant device (1) according to claim 1, wherein said predefined number of rows ranges from 10 to 20.

6. The glaucoma implant device (1) according to claim 1, wherein said mesh portion (11) has a height ranging from 10 μm to 50 μm in height,
   wherein said perimetral sides have a width ranging from 15 μm to 40 μm, and
   wherein the diameter of said inner ducts (1111') ranges from 5 μm to 12 μm.

7. The glaucoma implant device (1) according to claim 1, wherein said openings (3111) define a width that ranges from 4 μm to 10 μm.

8. The glaucoma implant device (1) according to claim 1, wherein said polygonal cells (111) have a hollow hexagon shape to define, said liquid collecting area (2111).

9. The glaucoma implant device (1) according to claim 8, wherein said mesh portion (11) has a hexagon periodicity ranging from 80 μm to 200 μm.

10. The glaucoma implant device (1) according to claim 1, wherein said mesh portion (11) is convex such as to follow an eye curvature.

11. The glaucoma implant device (1) according to claim 1, wherein said connection portion (21) has a truncated cone shape with a portion having the greatest width and smallest height at said mesh portion (11).

12. The glaucoma implant device (1) according to claim 1 further comprising a stent portion (31) coupled to said connection portion (21),
    wherein said stent portion (31) is able to dilate said Schlemm canal and to direct aqueous humour from Schlemm canal to said connection portion (21), and
    wherein said connection portion (21) has a truncated cone shape with a portion having a smallest width and greatest height at said stent portion (31), wherein said greatest height is equal to the height of said stent portion (31).

13. The glaucoma implant device (1) according to claim 12, wherein said stent portion (31) is defined by an elongated element curved according to a radius of the Schlemm Canal,
    wherein an outer surface (131) of said stent portion (31) is provided with a plurality of apertures (231) defining a void area of said outer surface, wherein said void area is greater than the solid area of said outer surface, and
    wherein an inner portion of said stent portion (31) is provided with a stiffening structure (331) in contact with an inner surface of said outer surface (131) and defining a solid volume of said inner portion, wherein said inner portion has a void volume greater than said solid volume.

14. The glaucoma implant device (1) according to claim 12, wherein said stent portion (31) ranges from 3 mm to 8 mm in length, and
    wherein said stent portion (31) has an ellipsoid cross section having a major axis ranging from 200 μm to 400 μm.

15. The glaucoma implant device (1) according to claim 12, wherein said stent portion (31) and/or said connecting portion (21) are provided with a plurality of hollow microneedles (101; 102) configured to face said mesh portion, wherein the dimension in height of said hollow microneedles (101; 102) ranges from 20 µm to 40 µm.

* * * * *